US009139929B2

(12) United States Patent
Minoux et al.

(10) Patent No.: US 9,139,929 B2
(45) Date of Patent: Sep. 22, 2015

(54) DEHYDRATION OF ALCOHOLS ON A CRYSTALLINE SILICATE OF LOW SI/AL RATIO

(75) Inventors: Delphine Minoux, Nivelles (BE); Nikolai Nesterenko, Nivelles (BE); Cindy Adam, Wierde (BE); Sander Van Donk, Sainte-Adresse (FR); Walter Vermeiren, Houthalen (BE)

(73) Assignee: TOTAL RESEARCH & TECHNOLOGY FELUY, Seneffe (BE)

( * ) Notice: Subject to any disclaimer, the term of this patent is extended or adjusted under 35 U.S.C. 154(b) by 117 days.

(21) Appl. No.: 13/522,619

(22) PCT Filed: Jan. 21, 2011

(86) PCT No.: PCT/EP2011/050855
§ 371 (c)(1),
(2), (4) Date: Oct. 8, 2012

(87) PCT Pub. No.: WO2011/089235
PCT Pub. Date: Jul. 28, 2011

(65) Prior Publication Data
US 2013/0041196 A1    Feb. 14, 2013

(30) Foreign Application Priority Data

Jan. 22, 2010 (EP) .................................. 10151355
Jan. 26, 2010 (EP) .................................. 10151633

(51) Int. Cl.
C07C 1/22 (2006.01)
C25D 7/06 (2006.01)
C23C 18/00 (2006.01)
C25D 17/00 (2006.01)

(52) U.S. Cl.
CPC .............. *C25D 7/0664* (2013.01); *C23C 18/00* (2013.01); *C25D 17/00* (2013.01)

(58) Field of Classification Search
CPC ................................................ C07C 1/20–1/29
USPC ............ 585/638–642; 502/60, 61, 62, 63, 64, 502/208, 209, 210, 211, 212, 213, 214; 208/43, 133, 141
See application file for complete search history.

(56) References Cited

U.S. PATENT DOCUMENTS 3,911,041 A * 10/1975 Kaeding et al. ................ 585/711
4,550,217 A * 10/1985 Graziani et al. .............. 585/324
(Continued)

FOREIGN PATENT DOCUMENTS

EP        2090561 A1    8/2009
JP        2009-215244 A    9/2009

*Primary Examiner* — In Suk Bullock
*Assistant Examiner* — Sharon Pregler

(57) ABSTRACT

The present invention (in a first embodiment) relates to a process for the dehydration of an alcohol having at least 2 carbon atoms to make the corresponding olefin, comprising: introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B),
Wherein,
the catalyst is a crystalline silicate of the group FER, MWW, EUO, MFS, ZSM-48, MTT or TON having Si/Al under 100,
or a dealuminated crystalline silicate of the group FER, MWW, EUO, MFS, ZSM-48, MTT or TON having Si/Al under 100,
or a phosphorus modified crystalline silicate of the group FER, MWW, EUO, MFS, ZSM-48, MTT or TON having Si/Al under 100,
the WHSV of the alcohol is at least 4 h$^{-1}$ and/or the temperature ranges from 320° C. to 600° C.

23 Claims, 1 Drawing Sheet

(56) References Cited

U.S. PATENT DOCUMENTS 4,590,320 A * 5/1986 Sapre .................. 585/324
4,727,214 A * 2/1988 Uytterhoeven et al. ....... 585/640
2011/0124939 A1 5/2011 Minoux et al.

* cited by examiner

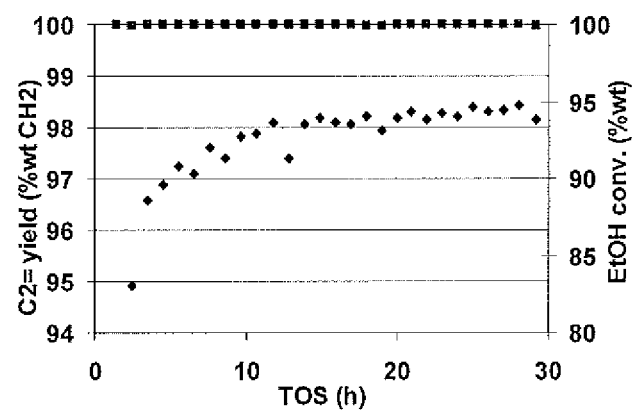

DEHYDRATION OF ALCOHOLS ON A CRYSTALLINE SILICATE OF LOW SI/AL RATIO

CROSS-REFERENCE TO RELATED APPLICATIONS

This application claims the benefit of PCT/EP2011/050855, filed Jan. 21, 2011, which claims priority from EP 10151355.4, filed Jan. 22, 2010 and EP 10151633.4, filed Jan. 26, 2010.

FIELD OF THE INVENTION

The present invention relates to the dehydration of at least an alcohol on a crystalline silicate of low Si/Al ratio to make the corresponding olefin. The limited supply and increasing cost of crude oil has prompted the search for alternative processes for producing hydrocarbon products such as ethylene. Ethanol can be obtained by fermentation of carbohydrates. Made up of organic matter from living organisms, biomass is the world's leading renewable energy source.

BACKGROUND OF THE INVENTION

U.S. Pat. No. 4,727,214 describes a process for converting anhydrous or aqueous ethanol into ethylene by means of a catalyst of the crystalline zeolite type, said catalyst having, on the one hand, channels or pores formed by cycles or rings of oxygen atoms having 8 and/or 10 elements or members, and on the other hand, an atomic Si/Al ratio of less than about 20. In the examples, the atomic ratio Si/Al of the FER used is from 5 to 20, the temperature from 217 to 280° C., and the WHSV of 2.5 $h^{-1}$.

JP 2009-215244 A published on 24 Sep. 2009 relates to a method to produce ethylene by contacting ethanol on a H-FER catalyst, having an atomic Si/Al between 3 and 20, more specifically between 4 and 10, sodium and potassium contents both of 0.1% wt or less, more specifically of 0.005% wt or less, the temperature ranging from 200 to 300° C., pressure from 10 to 100 bara, and WHSV from 0.1 to 10 $h^{-1}$. In examples, the appraisal of the ethanol reaction is achieved by method of gas pulse reaction using gas chromatograph. In the examples the temperature is 260° C. or under.

WO 2009-098262 (in a first embodiment) relates to a process for the dehydration of an alcohol having at least 2 carbon atoms to make the corresponding olefin, comprising:
introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B),
Wherein
the catalyst is:
    a crystalline silicate having a ratio Si/Al of at least about 100, or
    a dealuminated crystalline silicate, or
    a phosphorus modified zeolite,
the WHSV of the alcohols is at least 2 $h^{-1}$,
the temperature ranges from 280° C. to 500° C.

WO 2009-098262 (in a second embodiment) relates to a process for the dehydration of an alcohol having at least 2 carbon atoms to make the corresponding olefin, comprising:
introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B),
Wherein
the catalyst is a phosphorus modified zeolite,
the temperature ranges from 280° C. to 500° C.

It has now been discovered that the dehydration of at least an alcohol to the corresponding olefin made on:
a crystalline silicate of the group FER, MWW, EUO, MFS, ZSM-48, MTT or TON having Si/Al under 100,
or a dealuminated crystalline silicate of the group FER, MWW, EUO, MFS, ZSM-48, MTT or TON having Si/Al under 100,
or a phosphorus modified crystalline silicate of the group FER, MWW, EUO, MFS, ZSM-48, MTT or TON having Si/Al under 100,
has many advantages. Said dehydration is made with a WHSV of at least 4 $h^{-1}$ or at a temperature from 320 to 600° C.

By way of example, in the dehydration of ethanol on a ferrierite having a Si/Al ratio from 10 to 90 and with a WHSV of at least 4 $h^{-1}$ to make ethylene, the ethanol conversion is at least 98% and often 99%, advantageously the ethylene yield is at least 97%, the ethylene selectivity is at least 96% and often 97% and the ethylene purity is at least 99% and often 99.8%.

The ethanol conversion is the ratio (ethanol introduced in the reactor—ethanol leaving the reactor)/(ethanol introduced in the reactor).
The ethylene yield is the ratio, on carbon basis, (ethylene leaving the reactor)/(ethanol introduced in the reactor).
The ethylene selectivity is the ratio, on carbon basis, (ethylene leaving the reactor)/(ethanol converted in the reactor).

The ethylene purity is the ratio, on carbon basis, (ethylene leaving the reactor)/(ethylene+ethane leaving the reactor). It means the ethylene purity is the percentage of ethylene, on a carbon basis, present in the $C_2$ cut, containing close-boiling compounds, recovered in the stream leaving the reactor. The $C_2$ cut doesn't comprise the unconverted ethanol and acetaldehyde if any. The same definitions apply mutatis mutandis to the alcohol and the olefin.

BRIEF SUMMARY OF THE INVENTION

The present invention (in a first embodiment) relates to a process for the dehydration of an alcohol having at least 2 carbon atoms to make the corresponding olefin, comprising:
introducing in a reactor a stream (A) comprising at least an alcohol, optionally water, optionally an inert component, contacting said stream with a catalyst in said reactor at conditions effective to dehydrate at least a portion of the alcohol to make an olefin,
recovering from said reactor an olefin containing stream (B),
Wherein,
    the catalyst is a crystalline silicate of the group FER, MWW, EUO, MFS, ZSM-48, MTT or TON having Si/Al under 100,
    or a dealuminated crystalline silicate of the group FER, MWW, EUO, MFS, ZSM-48, MTT or TON having Si/Al under 100,
    or a phosphorus modified crystalline silicate of the group FER, MWW, EUO, MFS, ZSM-48, MTT or TON having Si/Al under 100,
the WHSV of the alcohol is at least 4 $h^{-1}$.

The present invention (in a second embodiment) also relates to a process for the dehydration of an alcohol having at least 2 carbon atoms to make the corresponding olefin, comprising:

introducing in a reactor a stream (A) comprising at least an alcohol, optionally water, optionally an inert component, contacting said stream with a catalyst in said reactor at conditions effective to dehydrate at least a portion of the alcohol to make an olefin, recovering from said reactor an olefin containing stream (B), Wherein, the catalyst is a crystalline silicate of the group FER, MWW, EUO, MFS, ZSM-48, MTT or TON having Si/Al under 100, or a dealuminated crystalline silicate of the group FER, MWW, EUO, MFS, ZSM-48, MTT or TON having Si/Al under 100, or a phosphorus modified crystalline silicate of the group FER, MWW, EUO, MFS, ZSM-48, MTT or TON having Si/Al under 100, the temperature ranges from 320° C. to 600° C.

It is worth to note that a crystalline silicate having an atomic Si/Al ratio under 100, according to the invention can be obtained by synthesis without subjecting it to dealumination by any means.

DETAILED DESCRIPTION OF THE INVENTION

As regards the stream (A), The alcohol is any alcohol provided it can be dehydrated to the corresponding olefin. By way of example mention may be made of alcohols having from 2 to 10 carbon atoms. Advantageously the invention is of interest for ethanol, propanol, butanol and phenylethanol.

The alcohol may be subjected to dehydration alone or in mixture with an inert medium. The inert component is any component provided there is no adverse effect on the catalyst. Because the dehydration is endothermic the inert component can be used to bring energy. The inert component may be selected among the saturated hydrocarbons having up to 10 carbon atoms, naphtenes, nitrogen and $CO_2$. Advantageously it is a saturated hydrocarbon or a mixture of saturated hydrocarbons having from 3 to 7 carbon atoms, more advantageously having from 4 to 6 carbon atoms and is preferably pentane. An example of inert component can be any individual saturated compound, a synthetic mixture of the individual saturated compounds as well as some equilibrated refinery streams like straight naphtha, butanes etc. Advantageously the inert component is a saturated hydrocarbon having from 3 to 6 carbon atoms and is preferably pentane. The weight proportions of respectively alcohol, water and inert component are, for example, 5-100/0-95/0-95 (the total being 100). The stream (A) can be liquid or gaseous.

As regards the reactor, it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

As regards the pressure, it can be any pressure but it is more easy and economical to operate at moderate pressure. By way of example the pressure of the reactor ranges from 0.5 to 30 bars absolute (50 kPa to 3 MPa), advantageously from 0.5 to 5 bars absolute (50 kPa to 0.5 MPa), more advantageously from 1.2 to 5 bars absolute (0.12 MPa to 0.5 MPa) and preferably from 1.2 to 4 bars absolute (0.12 MPa to 0.4 MPa). Advantageously the partial pressure of the alcohol is from 1.2 to 4 bars absolute (0.12 MPa to 0.4 MPa), more advantageously from 1.2 to 3.5 bars absolute (0.35 MPa).

As regards the temperature, and the first embodiment it ranges from 280° C. to 600° C., advantageously from 300° C. to 580° C., more advantageously from 350° C. to 580° C. As regards the temperature and the second embodiment it ranges from 320° C. to 600° C., advantageously from 320° C. to 580° C., more advantageously from 350° C. to 580° C.

These reaction temperatures refer substantially to average catalyst bed temperature. The ethanol dehydration is an endothermic reaction and requires the input of reaction heat in order to maintain catalyst activity sufficiently high and shift the thermodynamic equilibrium to sufficiently high conversion levels.

In case of fluidised bed reactors: (i) for stationary fluidised beds without catalyst circulation, the reaction temperature is substantially homogeneous throughout the catalyst bed; (ii) in case of circulating fluidised beds where catalyst circulates between a converting reaction section and a catalyst regeneration section, depending on the degree of catalyst backmixing the temperature in the catalyst bed approaches homogeneous conditions (a lot of backmixing) or approaches plug flow conditions (nearly no backmixing) and hence a decreasing temperature profile will install as the conversion proceeds.

In case of fixed bed or moving bed reactors, a decreasing temperature profile will install as the conversion of the alcohol proceeds. In order to compensate for temperature drop and consequently decreasing catalyst activity or approach to thermodynamic equilibrium, reaction heat can be introduced by using several catalyst beds in series with interheating of the reactor effluent from the first bed to higher temperatures and introducing the heated effluent in a second catalyst bed, etc. When fixed bed reactors are used, a multi-tubular reactor can be used where the catalyst is loaded in small-diameter tubes that are installed in a reactor shell. At the shell side, a heating medium is introduced that provides the required reaction heat by heat-transfer through the wall of the reactor tubes to the catalyst.

As regards the WHSV of the alcohol, and the first embodiment it ranges advantageously from 4 to 20 $h^{-1}$, preferably from 5 to 15 $h^{-1}$, more preferably from 7 to 12 $h^{-1}$. As regards the second embodiment it ranges advantageously from 2 to 20 $h^{-1}$, more advantageously from 4 to 20 $h^{-1}$, preferably from 5 to 15 $h^{-1}$, more preferably from 7 to 12 $h^{-1}$.

As regards the stream (B), it comprises essentially water, olefin, the inert component (if any) and unconverted alcohol. Said unconverted alcohol is supposed to be as less as possible. The olefin is recovered by usual fractionation means. Advantageously the inert component, if any, is recycled in the stream (A) as well as the unconverted alcohol, if any. Unconverted alcohol, if any, is recycled to the reactor in the stream (A).

As regards the catalyst, it is a crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MTT (ZSM-23) or TON (ZSM-22, Theta-1, NU-10), or a dealuminated crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MIT (ZSM-23) or TON (ZSM-22, Theta-1, NU-10), or a phosphorus modified crystalline silicate of the group FER (ferrierite, FU-9, ZSM-35), MWW (MCM-22, PSH-3, ITQ-1, MCM-49), EUO (ZSM-50, EU-1), MFS (ZSM-57), ZSM-48, MIT (ZSM-23) or TON (ZSM-22, Theta-1, NU-10).

About the crystalline silicate of FER structure (ferrierite, FU-9, ZSM-35) it can be the lamellar precursor which becomes FER by calcinations.

The Si/Al ratio is advantageously under 100 and at least 10. In an embodiment the Si/Al ratio is advantageously under 100 and at least 20.

The crystalline silicate is such as the Si/Al ratio ranges more advantageously from 10 to 90, preferably from 20 to 90, more preferably from 25 to 90 and much more preferably from 30 to 90.

The acidity of the catalyst can be determined by the amount of residual ammonia on the catalyst following contact of the catalyst with ammonia which adsorbs to the acid sites on the catalyst with subsequent ammonium desorption at elevated temperature measured by differential thermogravimetric analysis.

The crystalline silicate can be subjected to various treatments before use in the dehydration including, ion exchange, modification with metals (in a not restrictive manner alkali, alkali-earth, transition, or rare earth elements), external surface passivation, modification with P-compounds, steaming, acid treatment or other dealumination methods, or combination thereof.

In a specific embodiment the crystalline silicate is steamed to remove aluminium from the crystalline silicate framework. The steam treatment is conducted at elevated temperature, preferably in the range of from 425 to 870° C., more preferably in the range of from 540 to 815° C. and at atmospheric pressure and at a water partial pressure of from 13 to 200 kPa. Preferably, the steam treatment is conducted in an atmosphere comprising from 5 to 100% steam. The steam atmosphere preferably contains from 5 to 100 vol % steam with from 0 to 95 vol % of an inert gas, preferably nitrogen. A more preferred atmosphere comprises 72 vol % steam and 28 vol % nitrogen i.e. 72 kPa steam at a pressure of one atmosphere. The steam treatment is preferably carried out for a period of from 1 to 200 hours, more preferably from 20 hours to 100 hours. As stated above, the steam treatment tends to reduce the amount of tetrahedral aluminium in the crystalline silicate framework, by forming alumina.

In a more specific embodiment the crystalline silicate is dealuminated by heating the catalyst in steam to remove aluminium from the crystalline silicate framework and extracting aluminium from the catalyst by contacting the catalyst with a complexing agent for aluminium to remove from pores of the framework alumina deposited therein during the steaming step thereby to increase the silicon/aluminium atomic ratio of the catalyst. In accordance with the present invention, the commercially available crystalline silicate is modified by a steaming process which reduces the tetrahedral aluminium in the crystalline silicate framework and converts the aluminium atoms into octahedral aluminium in the form of amorphous alumina. Although in the steaming step aluminium atoms are chemically removed from the crystalline silicate framework structure to form alumina particles, those particles cause partial obstruction of the pores or channels in the framework. This could inhibit the dehydration process of the present invention. Accordingly, following the steaming step, the crystalline silicate is subjected to an extraction step wherein amorphous alumina is removed from the pores and the micropore volume is, at least partially, recovered. The physical removal, by a leaching step, of the amorphous alumina from the pores by the formation of a water-soluble aluminium complex yields the overall effect of de-alumination of the crystalline silicate. In this way by removing aluminium from the crystalline silicate framework and then removing alumina formed therefrom from the pores, the process aims at achieving a substantially homogeneous de-alumination throughout the whole pore surfaces of the catalyst. This reduces the acidity of the catalyst. The reduction of acidity ideally occurs substantially homogeneously throughout the pores defined in the crystalline silicate framework. Following the steam treatment, the extraction process is performed in order to de-aluminate the catalyst by leaching. The aluminium is preferably extracted from the crystalline silicate by a complexing agent which tends to form a soluble complex with alumina. The complexing agent is preferably in an aqueous solution thereof. The complexing agent may comprise an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The complexing agent may comprise an inorganic acid such as nitric acid, halogenic acids, sulphuric acid, phosphoric acid or salts of such acids or a mixture of such acids. The complexing agent may also comprise a mixture of such organic and inorganic acids or their corresponding salts. The complexing agent for aluminium preferably forms a water-soluble complex with aluminium, and in particular removes alumina which is formed during the steam treatment step from the crystalline silicate. A particularly preferred complexing agent may comprise an amine, preferably ethylene diamine tetraacetic acid (EDTA) or a salt thereof, in particular the sodium salt thereof.

Following the aluminium leaching step, the crystalline silicate may be subsequently washed, for example with distilled water, and then dried, preferably at an elevated temperature, for example around 110° C.

Additionally, if during the preparation of the catalysts of the invention alkaline or alkaline earth metals have been used, the molecular sieve might be subjected to an ion-exchange step. Conventionally, ion-exchange is done in aqueous solutions using ammonium salts or inorganic acids.

Following the de-alumination step, the catalyst is thereafter calcined, for example at a temperature of from 400 to 800° C. at atmospheric pressure for a period of from 1 to 10 hours.

In another specific embodiment the crystalline silicate is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicates, metal oxides such as $ZrO_2$ and/or metals, or gels including mixtures of silica and metal oxides. If the binder which is used in conjunction with the crystalline silicate is itself catalytically active, this may alter the conversion and/or the selectivity of the catalyst. Inactive materials for the binder may suitably serve as diluents to control the amount of conversion so that products can be obtained economically and orderly without employing other means for controlling the reaction rate. It is desirable to provide a catalyst having a good crush strength. This is because in commercial use, it is desirable to prevent the catalyst from breaking down into powder-like materials. Such clay or oxide binders have been employed normally only for the purpose of improving the crush strength of the catalyst. A particularly preferred binder for the catalyst of the present invention comprises silica. The relative proportions of the finely divided crystalline silicate material and the inorganic oxide matrix of the binder can vary widely. Typically, the binder content ranges from 5 to 95% by weight, more typically from 20 to 50% by weight, based on the weight of the composite catalyst. Such a mixture of the crystalline silicate and an inorganic oxide binder is referred to as a formulated crystalline silicate. In mixing the catalyst with a binder, the catalyst may be formulated into pellets, extruded into other shapes, or formed into spheres or a spray-dried powder. Typically, the binder and the crystalline silicate are mixed together by a mixing process. In such a process, the binder, for example silica, in the form of a gel is mixed with the crystalline silicate material and the resultant mixture is extruded into the desired shape, for example cylindic or multi-lobe bars. Spherical shapes can be made in rotating granulators or by oil-drop technique. Small spheres can further be made by spray-drying a catalyst-binder suspension. Thereafter, the formulated crystalline silicate is calcined in air or an inert gas, typically at a temperature of from 200 to 900° C. for a period of from 1 to 48 hours. The binder preferably does not contain any aluminium compounds, such as alumina. This is because as mentioned above the preferred catalyst for use in the invention is de-aluminated to increase the silicon/aluminium ratio of the crystalline silicate. The presence of alumina in the binder yields other excess alumina if the binding step is performed prior to the aluminium extraction step. If the aluminium-containing binder is mixed with the crystalline silicate following aluminium extraction, this re-aluminates the catalyst.

In addition, the mixing of the catalyst with the binder may be carried out either before or after the steaming and extraction steps.

One skilled in the art will also appreciate that the olefins made by the dehydration process of the present invention can be, by way of example, polymerized. When the olefin is ethylene it can be, by way of example, polymerized to form polyethylenes,
dimerized to butene and then isomerised to isobutene, said isobutene reacting with ethanol to produce ETBE,
dimerised to 1-butene, trimerised to 1-hexene or tetramerised to 1-octene, said alpha-olefins comonomers are further reacted with ethylene to produce polyethylene
dimerised to 1-butene, said 1-butene is isomerised to 2-butene and said 2-butene is further converted with ethylene by metathesis reaction into propylene and said propylene can be polymerised to polypropylene,
converted to ethylene oxide and glycol or
converted to vinyl chloride.
The present invention relates also to said polyethylenes, polypropylene, propylene, butene, hexane, octene, isobutene, ETBE, vinyl chloride, ethylene oxide and glycol.

EXAMPLES

Experimental

The stainless-steel reactor tube has an internal diameter of 10 mm. 10 ml of catalyst, as pellets of 35-45 mesh, is loaded in the tubular reactor. The void spaces before and after the catalyst are filled with SiC granulated of 2 mm. The temperature profile is monitored with the aid of a thermocouple well placed inside the reactor. The reactor temperature is increased at a rate of 60° C./h to 550° C. under air, kept 2 hours at 550° C. and then purged by nitrogen. The nitrogen is then replaced by the feed (either a pure ethanol feed or an aqueous ethanol feed).

The catalytic tests are then performed down-flow, at near atmospheric pressure (pressure of 1.35 bara), in a temperature range of 300-450° C. and with a weight hour space velocity (WHSV) varying from 2 to 10 $h^{-1}$.
Analysis of the products is performed by using an on-line gas chromatography.

Example (According to the Invention)

The catalyst used here is a crystalline silicate of the FER structure. The H-FER has a Si/Al of 33 under powder form.
An ethanol/water mixture at the azeotropic composition (95/5) % wt has been processed on the catalyst under 2 bara, at 400° C., and with an ethanol space velocity of 7 $h^{-1}$.
In this set of operating conditions, ethanol conversion is almost complete, with a $C_2^=$ selectivity of 97.5% wt $CH_2$, and a $C_2^=$ purity above 99.8%. Low amounts of $C_4$ compounds are formed.
The results are on FIG. 1 and on the following table.

| FEED | EtOH/H2O (95/5) % wt |
|---|---|
| P (bara) | 2 |
| T (° C.) | 400 |
| WHSV (H-1) | 7 |
| EtOH conversion (% wt CH2) | 99.97 |
| DEE | 0.0 |
| Acetaldyde | 0.42 |
| Yield on C-basis (% wt CH2) | |
| CH4 | 0.0 |
| C2 | 0.16 |
| C2= | 97.5 |
| C3= | 0.1 |
| C4+ olef | 1.7 |
| C4+ paraf | 0.0 |
| Aromatics | 0.0 |
| Unknown | 0.03 |
| Selectivity on C-basis (% wt CH2) | |
| CH4 | 0.0 |
| C2 | 0.16 |
| C2= | 97.5 |
| C3= | 0.1 |
| C4+ olef | 1.7 |
| C4+ paraf | 0.0 |
| Aromatics | 0.0 |
| Unknown | 0.03 |
| C2's purity (%) | 99.84 |

The invention claimed is:
1. A process for the dehydration of an alcohol having at least 4 carbon atoms to make the corresponding olefin, comprising:
  introducing in a reactor a stream (A) comprising at least an alcohol having at least 4 carbon atoms, optionally water, optionally an inert component, contacting said stream with a catalyst in said reactor at conditions effective to dehydrate at least a portion of the alcohol to make a corresponding olefin,
  recovering from said reactor an olefin containing stream (B),
  wherein,
    the catalyst is a crystalline silicate of the group FU-9, MWW, EUO, MFS, or TON having Si/Al of at least 20 and under 100,
    or a dealuminated crystalline silicate of the group FU-9, MWW, EUO, MFS, or TON having Si/Al of at least 20 and under 100, or a phosphorus modified crystalline silicate of the group FU-9, MWW, EUO, MFS, or TON having Si/Al of at least 20 and under 100, and wherein the WHSV of the alcohol is at least 4 h$^{-1}$, and wherein the pressure of the reactor ranges from 0.5 to 30 bars absolute (50 kPa to 3 MPa).

2. The process according to claim 1 wherein WHSV is from 4 to 20 h$^{-1}$.

3. The process according to claim 1 wherein the temperature of the dehydration catalyst ranges from 280° C. to 600° C.

4. A process for the dehydration of an alcohol having from 5 to 10 carbon atoms to make the corresponding olefin, comprising:

introducing in a reactor a stream (A) comprising at least an alcohol having from 5 to 10 carbon atoms, optionally water, optionally an inert component, contacting said stream with a catalyst in said reactor at conditions effective to dehydrate at least a portion of the alcohol to make a corresponding olefin, recovering from said reactor an olefin containing stream (B), wherein, the catalyst is a crystalline silicate of the group FER, MWW, EUO, MFS, ZSM-48, MTT, or TON having Si/Al of at least 20 and under 100, or a dealuminated crystalline silicate of the group FER, MWW, EUO, MFS, ZSM-48, MTT, or TON having Si/Al of at least 20 and under 100, or a phosphorus modified crystalline silicate of the group FER, MWW, EUO, MFS, ZSM-48, MTT, or TON having Si/Al of at least 20 and under 100, and wherein the temperature ranges from 320° C. to 600° C., and wherein the pressure of the reactor ranges from 0.5 to 30 bars absolute (50 kPa to 3 MPa).

5. The process according to claim 4 wherein the WHSV ranges from 2 to 20 h$^{-1}$.

6. The process according to claim 4 wherein the temperature of the dehydration catalyst ranges from 320° C. to 600° C.

7. The process according to claim 4 wherein the Si/Al ratio of the crystalline silicate ranges from 10 to 90.

8. The process according to claim 4 wherein the crystalline silicate is steamed to remove aluminium from the crystalline silicate framework.

9. The process according to claim 8 wherein, further to the steaming, aluminium is extracted from the catalyst by contacting the catalyst with a complexing agent for aluminium to remove from pores of the framework alumina deposited therein during the steaming step thereby to increase the silicon/aluminium atomic ratio of the catalyst.

10. The process according to claim 4 wherein the pressure of the reactor ranges from 0.5 to 5 bars absolute.

11. The process according to claim 4 wherein the partial pressure of the alcohol in the dehydration reactor ranges from 1.2 to 4 bars absolute (0.12 MPa to 0.4 MPa).

12. The process according to claim 4 wherein the crystalline silicate is subjected to various treatments before use in the dehydration including, ion exchange, modification with metals external surface passivation, modification with P-compounds, steaming, acid treatment or other dealumination methods, or combination thereof.

13. The process according to claim 1 wherein WHSV is from 5 to 15 h$^{-1}$.

14. The process according to claim 1 wherein WHSV is from 7 to 12 h$^{-1}$.

15. The process according to claim 1 wherein the temperature of the dehydration catalyst ranges from 300° C. to 580° C.

16. The process according to claim 1 wherein the temperature of the dehydration catalyst ranges from 350° C. to 580° C.

17. The process according to claim 1, wherein the catalyst is the crystalline silicate, the dealuminated crystalline silicate, or the phosphorus modified crystalline silicate of the group FU-9, MWW, EUO, MFS, Theta-1, or NU-10 having Si/Al of at least 20 and under 100.

18. The process according to claim 1, wherein the catalyst is the crystalline silicate, the dealuminated crystalline silicate, or the phosphorus modified crystalline silicate of the group MWW, EUO, MFS, Theta-1, or NU-10 having Si/Al of at least 20 and under 100.

19. The process according to claim 1, wherein the catalyst is the crystalline silicate, the dealuminated crystalline silicate, or the phosphorus modified crystalline silicate of the group MWW, EUO, MFS, having Si/Al of at least 20 and under 100.

20. A process for the dehydration of an alcohol having at least 4 carbon atoms to make the corresponding olefin, comprising:

introducing in a reactor a stream (A) comprising at least an alcohol having at least 4 carbon atoms, optionally water, optionally an inert component, contacting said stream with a catalyst in said reactor at conditions effective to dehydrate at least a portion of the alcohol to make a corresponding olefin, recovering from said reactor an olefin containing stream (B), wherein the catalyst is a phosphorus modified crystalline silicate of the group FER, MWW, EUO, MFS, ZSM-48, MTT, or TON having Si/Al of at least 20 and under 100, and wherein the temperature ranges from 320° C. to 600° C. or the WHSV of the alcohol is at least 4 h$^{-1}$, and wherein the partial pressure of the alcohol in the dehydration reactor ranges from 1.2 to 4 bars absolute (0.12 MPa to 0.4 MPa).

21. The process according to claim 1, wherein the alcohol is ethanol, and wherein ethanol conversion is at least 98%.

22. The process according to claim 1 wherein the alcohol is ethanol and the olefin is ethylene, and wherein ethylene yield is at least 97%.

23. The process according to claim 1 wherein the alcohol is ethanol and the olefin is ethylene, and wherein ethylene selectivity is at least 96%.

\* \* \* \* \*